United States Patent [19]

McRae

[11] Patent Number: Plant 5,950

[45] Date of Patent: Apr. 21, 1987

[54] ASIATIC LILY NAMED BRAVO

[75] Inventor: Edward A. McRae, Boring, Oreg.

[73] Assignee: Melridge, Inc., Gresham, Oreg.

[21] Appl. No.: 710,588

[22] Filed: Mar. 11, 1985

[51] Int. Cl.[4] ..... A01H 5/00
[52] U.S. Cl. ..... Plt./68
[58] Field of Search ..... Plt./68

*Primary Examiner*—James R. Feyrer
*Attorney, Agent, or Firm*—Charles W. Rummler; John B. Lungmus

[57] ABSTRACT

A new variety of hybrid Asiatic Lily bearing flowers of large size and excellent form particularly distinguished by their unusual red to red-orange color on the upper side and a deeper colored reverse side and by their large-sized and unusually broad tepals. The color of this flower is unique in the upright Asiatic division of lilies and the flowers are noted for long persistence, both on the plant and as cut-flowers. The new plant is highly resistant to disease, shows high tolerance to virus, making it an excellent garden plant, and has bulbs which may be precooled and forced for cut-flower production.

1 Drawing Figure

BACKGROUND OF THE INVENTION

This new variety of lily plant originated as a seedling selected from a group of seedlings resulting from my crossing of the cultivar "Showboat" U.S. Plant Pat. No. 4,177) with the cultivar "Red Carpet" (unpatented) in the course of breeding efforts carried on by me since 1975 at Sandy, Oreg., with the object of producing superior upright-flowering Asiatic lilies in the shades of red, suited to cut-flower production.

This new variety of lily plant was asexually reproduced by me and under my direction at Sandy, Oreg., and successive generations produced by bulk scale propagation and natural propagation from bulblets have demonstrated that this new lily plant possesses all of the desired characteristics of form, color, and habit; is a vigorous and good grower and propagator, and has the desirable characteristics of hybrid vigor, great hardiness, and a high degree of disease resistance as observed in western Oregon. Successive generations of this new plant produced by bulb scale propagation and natural propagation from bulblets have demonstrated that the novel and distinctive character of my new variety holds true under asexual propagation from generation to generation and appears to be firmly fixed.

DESCRIPTION OF THE DRAWING

This new variety of lily plant is illustrated in the accompanying photographic drawing, which shows a full face view of the open bloom together with several buds in various stages of development and illustrates the flower form, the arrangement of its unusually broad tepals and lack of spotting, the face view of the flower having been hand-painted to show the novel and distinctive orange-red to red color tone of the flower as herein specified.

DESCRIPTION OF THE NEW PLANT

The following is a detailed description of my new variety of Asiatic hybrid lily with color designations according to The R.H.S. Colour Chart published by The Royal Horticultural Society of London, England, and with nomenclature according to The International Lily Register of The Royal Horticultural Society.

THE PLANT

Origin: Seedling.

Parentage:

*Seed parent.*—"Showboat" (U.S. Plant Pat. No. 4,177).

*Pollen parent.*—"Red Carpet" (unpatented).

Classification:

*Botanic.*—Hybrid lily cultivar, Division I-A of The Royal Horticultural Society Horticultural Classification of Lilies.

*Commercial.*—Upright Asiatic hybrid lily.

Form: Single stem, erect and stately.

Height: About 75 to 100 cm. from bulbs about 12 to 15 cm. in circumference.

Growth: Vigorous and upright.

Foliage:

*Quantity.*—Abundant.

*Size of leaf.*—About 5 to 8 cm. long and about 1.5 to 2 cm. wide at the base.

*Leaf shape.*—Lanceolate and sessile, with acute tip and entire margins.

*Texture.*—Leathery.

*Aspect.*—Glossy.

*Color.*—Dark green.

Bulbs:

*Size.*—Ranging up to 25 cm. in circumference in commercial use.

*Color.*—White.

THE BUD

Form: Ovoid to oblong with obtuse base and tip.

Opening rate: The bud opens slowly at maturity in response to light.

Color: Deep red to more crimson red at tip ends, this color pattern being evident when the outer tepals first divide and when the tepals begin to unfurl.

Peduncle:

*Length.*—About 7 to 10 cm., depending upon light levels.

*Color.*—Green overlaid with plum.

THE FLOWER

Blooming habit: Annually, once and profusely, in mid-season for Asiatic lilies. October-dug bulbs, properly precooled, planted under glass in western Oregon and with no supplemental lighting, flower in an average of 70 to 85 days when grown at moderate temperatures.

Size: Large; about 16 to 18 cm. in diameter.

Borne: As a compact raceme or umbel with 5 to 7 blooms on a single stem.

Shape: Generally flat.

Tepalage:

*Number.*—Six.

*Arrangement.*—Upper tepals overlap the lower tepals about midway between them.

*Shape.*—Generally ovate, terminating in an acute tip and having entire margins.

*Color.*—The overall base color is Orange-Red, RHS 31A, particularly in the central portion, becoming a vibrant Red to Red-Orange, RHS 39A, in the end portions of the tepals. The reverse side of the tepals is a deeper Red overall, RHS 39A, with an overlay of slightly more Crimson Red, RHS 47B, on the midribs.

Maculation: The flowers are unspotted.

Color change: The flowers may become an overall lighter Orange-Red, RHS 31A, as it ages, especially if kept under low light levels.

Tepal longevity: Tepals stay on the stem about three weeks.

Pedicels:

*Length.*—About 8 to 15 cm. Secondary buds have shorter pedicels.

*Form.*—Sturdy.

*Color.*—Dark green with plum overlay.

Fragrance: None.

Lasting quality: The flower is long lasting both on the plant and as a cut-flower.

Disease resistance: The flower and plant are resistant to disease and in particular, resistant to Fusarium and Botrytis as observed in western Oregon.

THE REPRODUCTIVE ORGANS

Stamens:

*Number.*—Six.

*Arrangement.*—Typical of genus Lilium.

Filaments:

*Length.*—About 5 cm.

*Color.*—Orange-Red, RHS 31A.

Anthers and pollen:

*Color.*—Greyed Red, RHS 178A.

Pistils:

*Number.*—One.

Style length: About 5 cm.

Stigma:

*Color.*—Soft orange-red.

Character of ovaries: Typical of genus Lilium.

THE FRUIT

Fertility: The fruit is fertile.

Shape: Ovoid.

Color at maturity: Soft brown, sometimes overlaid with light plum.

My new Asiatic hybrid lily variety most nearly resembles the variety "Tabasco" (P.P.) but has spotless flowers of much larger size and with broader tepals. The flowers of the new plant are of a much lighter, more vibrant color, and they do not become brown-toned with age, as do those of "Tabasco". The inflorescence of this new variety is also more compact than that of "Tabasco".

I claim:

1. A new and distinct variety of Asiatic hybrid lily plant, substantially as herein shown and described, particularly distinguished by its vibrant red to red-orange coloring and its lack of spots providing a unique color pattern; the plant has vigorous growth and propagation characteristics; excellent flower form and substance; and has versatility both as a garden plant and as a plant produced from precooled bulbs forced for cut-flower production.

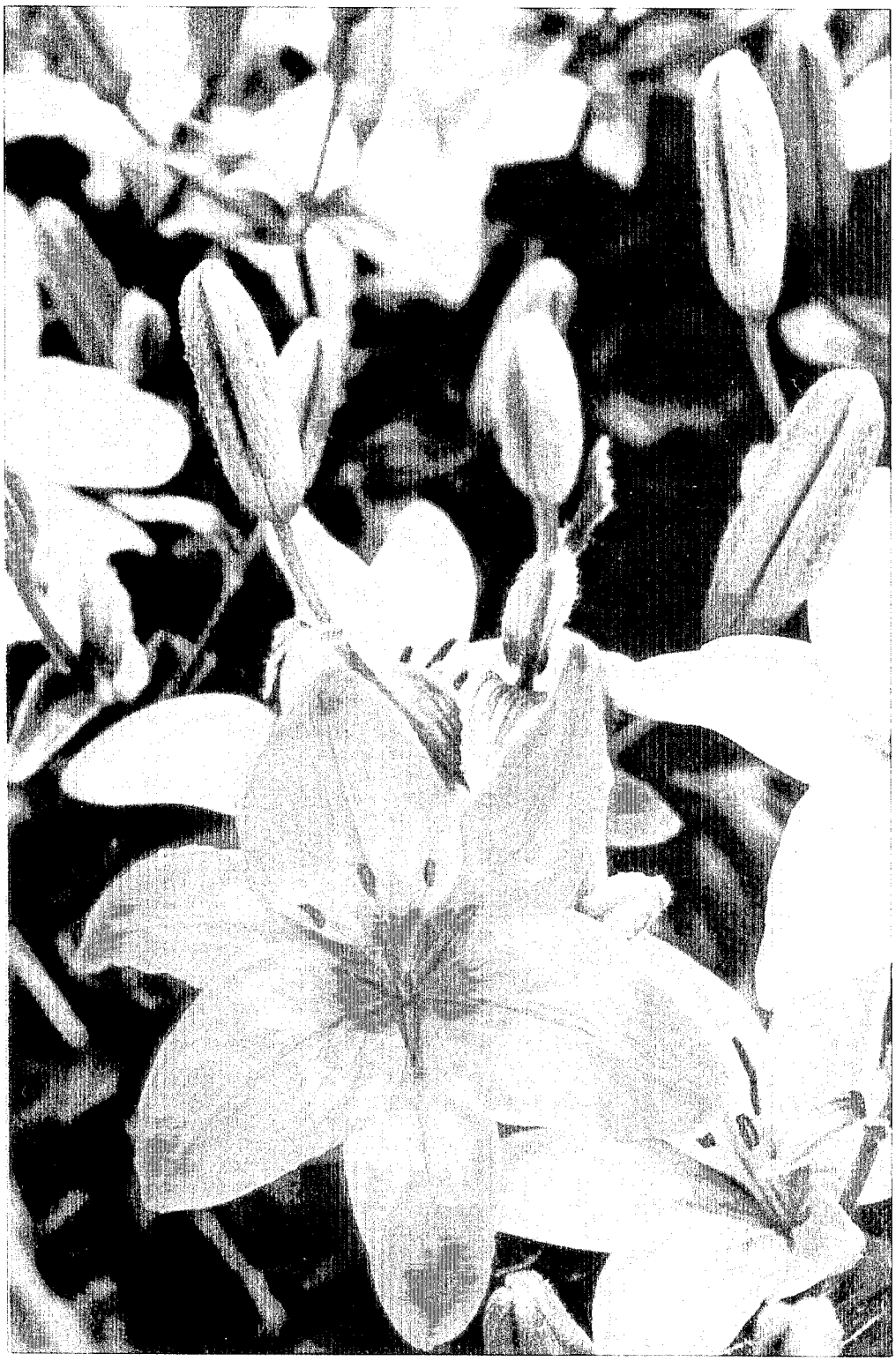

* * * * *